United States Patent
Mohan et al.

(10) Patent No.: US 9,839,721 B2
(45) Date of Patent: Dec. 12, 2017

(54) METHODS FOR DELIVERING SURGICAL GRAFTS TO A RESECTED TONSIL

(71) Applicant: Cook Biotech Incorporated, West Lafayette, IN (US)

(72) Inventors: P. Arun Mohan, West Lafayette, IN (US); Patrick Melder, Marietta, GA (US); Darin G. Schaeffer, Bloomington, IN (US); Andrew J. Kaucher, Lafayette, IN (US)

(73) Assignee: Cook Medical Technologies, LLC, Bloomington, IN (US)

( * ) Notice: Subject to any disclaimer, the term of this patent is extended or adjusted under 35 U.S.C. 154(b) by 492 days.

(21) Appl. No.: 13/865,298

(22) Filed: Apr. 18, 2013

(65) Prior Publication Data

US 2014/0148914 A1    May 29, 2014

Related U.S. Application Data

(60) Provisional application No. 61/635,272, filed on Apr. 18, 2012.

(51) Int. Cl.
*A61B 17/04* (2006.01)
*A61L 27/00* (2006.01)
(Continued)

(52) U.S. Cl.
CPC ...... *A61L 27/3604* (2013.01); *A61B 17/0469* (2013.01); *A61B 17/26* (2013.01);
(Continued)

(58) Field of Classification Search
CPC . A61B 17/0469; A61B 17/0482; A61B 17/04; A61B 17/062; A61B 17/26;
(Continued)

(56) References Cited

U.S. PATENT DOCUMENTS 3,604,071 A * 9/1971 Reimels ................ A61B 17/30
24/543
5,711,969 A   1/1998 Patel et al.
(Continued)

FOREIGN PATENT DOCUMENTS

WO   WO 2008/067085 A2   6/2008

OTHER PUBLICATIONS

C. Heeschen, et al., Nature Medicine 7 (2001), No. 7, 833-839.
C. Johnson et al., Circulation Research 94 (2004), No. 2, 262-268.

*Primary Examiner* — Christopher L Templeton
(74) *Attorney, Agent, or Firm* — Woodard, Emhardt, Moriarty, McNett & Henry, LLP

(57) ABSTRACT

Described are graft devices useful for treating surgical defects, delivery implements for delivery of the graft devices, combinations thereof, and methods for the preparation and use thereof. In certain aspects a tonsillectomy graft can include convexly curved outer edges, where the graft is sized and configured such that these outer edges reside proximate and along tonsillar pillars bounding a surgical tonsillectomy defect. The graft can include one or more pull tethers laced to the graft and functional to draw these outer edges toward one another when tensioned. The graft can be combined with a delivery implement having a delivery head and attached handle, where the delivery head is sized for receipt onto the tonsillectomy defect to deliver the graft. Additional product features, as well as associated methods, are also described.

31 Claims, 9 Drawing Sheets

(51) Int. Cl.
| | |
|---|---|
| *A61F 13/00* | (2006.01) |
| *A61B 17/24* | (2006.01) |
| *A61L 27/36* | (2006.01) |
| *A61B 17/26* | (2006.01) |
| *A61L 27/38* | (2006.01) |
| *A61B 17/00* | (2006.01) |

(52) U.S. Cl.
CPC ....... *A61L 27/3839* (2013.01); *A61B 17/0482* (2013.01); *A61B 17/24* (2013.01); *A61B 2017/00969* (2013.01); *A61B 2017/0495* (2013.01); *A61F 13/00012* (2013.01)

(58) Field of Classification Search
CPC .................. A61B 17/24; A61B 17/30; A61B 2017/00969; A61F 13/00012; A61F 2/0063; A61F 2002/0068; A61F 2002/0072; A61L 27/3604; A61L 27/3633; A61L 27/3839
See application file for complete search history.

(56) References Cited

U.S. PATENT DOCUMENTS

| | | | |
|---|---|---|---|
| 5,755,791 A | 5/1998 | Whitson et al. | |
| 5,824,010 A * | 10/1998 | McDonald | A61B 17/0482 606/148 |
| 5,855,619 A | 1/1999 | Caplan et al. | |
| 5,919,232 A * | 7/1999 | Chaffringeon | A61F 2/0063 424/423 |
| 5,925,064 A * | 7/1999 | Meyers | A61B 17/062 606/205 |
| 5,955,110 A | 9/1999 | Patel et al. | |
| 5,968,096 A | 10/1999 | Whitson et al. | |
| 6,206,931 B1 | 3/2001 | Cook et al. | |
| 6,648,921 B2 * | 11/2003 | Anderson | A61F 2/0045 600/37 |
| 6,730,102 B1 * | 5/2004 | Burdulis, Jr. | A61B 17/0469 606/144 |
| 6,746,458 B1 * | 6/2004 | Cloud | A61B 17/04 602/41 |
| 7,029,481 B1 * | 4/2006 | Burdulis, Jr. | A61B 17/0469 606/144 |
| 7,402,166 B2 * | 7/2008 | Feigl | A61B 17/0482 606/139 |
| 2002/0198543 A1 * | 12/2002 | Burdulis | A61B 17/0469 606/144 |
| 2003/0023316 A1 * | 1/2003 | Brown | A61F 2/0063 623/23.72 |
| 2004/0138747 A1 * | 7/2004 | Kaladelfos | A61F 2/0045 623/13.13 |
| 2005/0049638 A1 | 3/2005 | Mandelbaum | |
| 2007/0198039 A1 * | 8/2007 | Jones | A61F 5/0036 606/151 |
| 2008/0167519 A1 * | 7/2008 | St-Germain | A61F 2/0063 600/37 |
| 2008/0215070 A1 * | 9/2008 | Gildenberg | A61B 17/0483 606/148 |
| 2008/0255593 A1 * | 10/2008 | St-Germain | A61F 2/0063 606/151 |
| 2008/0286268 A1 * | 11/2008 | Johnson | A61L 27/3604 424/130.1 |
| 2009/0181074 A1 * | 7/2009 | Makower | A61L 15/42 424/447 |
| 2009/0228021 A1 * | 9/2009 | Leung | A61B 17/06166 606/139 |
| 2009/0275962 A1 * | 11/2009 | Zeiner | A61B 17/0469 606/151 |
| 2009/0326577 A1 | 12/2009 | Johnson et al. | |
| 2010/0106068 A1 | 4/2010 | Karpiel et al. | |
| 2011/0112513 A1 * | 5/2011 | Hester | A61B 17/06166 604/514 |
| 2012/0029532 A1 * | 2/2012 | Hodgkinson | A61B 17/0057 606/139 |
| 2012/0065649 A1 * | 3/2012 | Towler | A61F 2/0045 606/151 |

\* cited by examiner

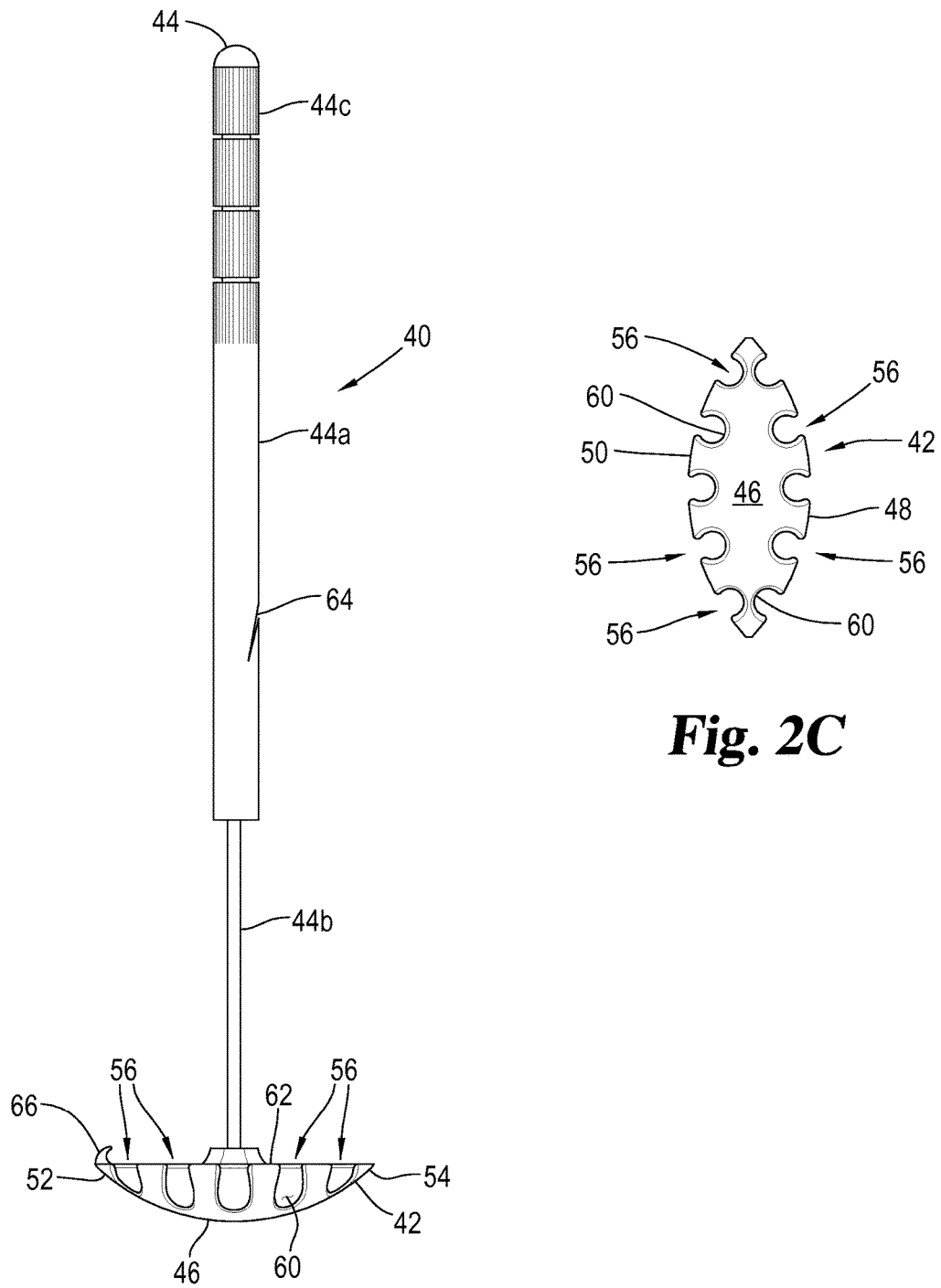

METHODS FOR DELIVERING SURGICAL GRAFTS TO A RESECTED TONSIL

REFERENCE TO RELATED APPLICATION

This application claims the benefit of U.S. Provisional Application No. 61/635,272, filed Apr. 18, 2012, which is hereby incorporated by reference.

BACKGROUND

The present invention relates generally to medical devices, methods and materials, and in certain aspects to medical grafts, delivery implements for medical grafts, combinations thereof, and methods for preparation and use thereof.

Many medical procedures require the treatment of a tissue defect in a patient, for example the defect can be either created surgically or present due to injury or disease. Examples occur in the removal of tonsils from patients, which leaves a surgical defect in the region of the resected tonsil and associated tissue. Such defects may be left uncovered to heal, potentially with the aid of sutures to gather and close the defect. In certain practices, such defects are treated with a graft material that is applied to the defect and secured in place, e.g. by sutures.

While some work has been done in this area, needs exist for improved and/or alternative grafting devices, graft delivery implements, and associated methods. Certain aspects of the present invention are addressed to these needs.

SUMMARY

In one aspect, the present invention provides a surgical tonsillectomy method that includes removing tissue from a patient, the tissue including at least one tonsil, so as to create a surgical defect. The method also includes applying to the surgical defect a graft including a decellularized animal tissue layer comprising submucosal tissue.

In another aspect, the present invention provides a surgical tonsillectomy method that includes removing tissue from a patient, the tissue including at least one tonsil, so as to create a surgical defect. The method also includes applying to the surgical defect a graft including a decellularized animal tissue layer comprising extracellular matrix tissue, and wherein said decellularized animal tissue layer retains at least one native growth factor.

In another aspect, the present invention provides a composition comprising a decellularized animal tissue layer comprising submucosal tissue, for use as a graft to treat a surgical defect created by removing tissue including at least one tonsil from a patient. The composition can be a multi-laminate construct including a plurality of said decellularized animal tissue layers, and/or the decellularized animal tissue layer can retain at least one native growth factor of the tissue layer.

In another aspect, the present invention provides a composition that includes a decellularized animal tissue layer comprising extracellular matrix tissue and retaining at least one native growth factor, for use as a graft to treat a surgical defect created by removing tissue including at least one tonsil from a patient.

In a further aspect, the present invention provides a graft device for treating a surgical tonsillectomy defect. The graft device includes a graft layer having a first convexly curved outer edge and an opposed second convexly curved outer edge, with the first and second convexly curved outer edges configured for approximation along anterior and posterior tonsillar pillars, respectively, bounding a surgical tonsillectomy defect. The graft device also includes one or more pull tethers connected to the graft layer and operable upon tensioning to move the first and second outer edges toward one another, in particularly beneficial embodiments during a folding of the graft layer. The one or more tethers can include at least one segment laced between a position proximate to the first convexly curved outer edge and a position proximate to the second convexly curved outer edge, and preferably a plurality of such laced segments.

The invention provides, in another aspect, a grafting apparatus for covering a surgical tonsillectomy defect. The grafting apparatus includes a graft delivery implement including a delivery head and a handle connected to the delivery head, the delivery head sized and configured for receipt onto a tonsillectomy defect between an anterior tonsillar pillar and a posterior tonsillar pillar. The delivery head includes a forward face for receiving a graft, and has a first lateral delivery head region and an opposed second lateral delivery head region. The first and second lateral delivery head regions each include a plurality of open-sided suturing slots extending inward from an outer edge of the delivery head. The grafting apparatus also includes a graft releasably held over the forward surface of the delivery head, the graft having a first lateral graft region positioned over the first lateral delivery head region and including a plurality of first suturable graft segments spanning across the open-sided suturing slots of the first lateral delivery head region and a second lateral graft region positioned over the second lateral delivery head region and including plurality of second suturable graft segments spanning across the open-sided suturing slots of the second lateral delivery head region. The grafting apparatus may also include one or more pull tethers connected to the graft and operable upon tensioning, after release of the graft from the delivery head, to move the first and second lateral graft regions toward one another, desirably during a folding movement of the graft.

In a further aspect, the invention provides a graft delivery implement for delivering a graft to a surgical tonsillectomy defect. The implement includes a handle and a delivery head connected to the handle. The delivery head is sized and configured for receipt onto a tonsillectomy defect between an anterior tonsillar pillar and a posterior tonsillar pillar. The delivery head includes a forward face for receiving a graft material, a first lateral delivery head region including a first plurality of open-sided suturing slots extending inward from an outer edge of the first lateral delivery head region, and a second lateral delivery head region opposite the first lateral delivery head region, the second lateral delivery head region including a second plurality of open-sided suturing slots extending inward from an outer edge of the second lateral delivery head region. The forward face of the delivery head can have a convexly curved surface. The delivery implement can include a barb member for engaging a graft material. The handle can define a tether retention slot. The outer edge of the first lateral delivery head region and the outer edge of the second lateral delivery head region can each be convexly curved. In further embodiments, such a graft delivery implement is combined with a graft device releasably held over the forward face of the delivery head, to provide a device for administering a graft.

Additional embodiments, as well as features and advantages thereof, will be apparent to those of ordinary skilled in the art from the descriptions herein.

BRIEF DESCRIPTION OF THE FIGURES

FIG. 2B provides a side view of the implement of FIG. 2A.

FIG. 2C provides a bottom end view of the implement of FIG. 2B.

DETAILED DESCRIPTION

Figure 1:
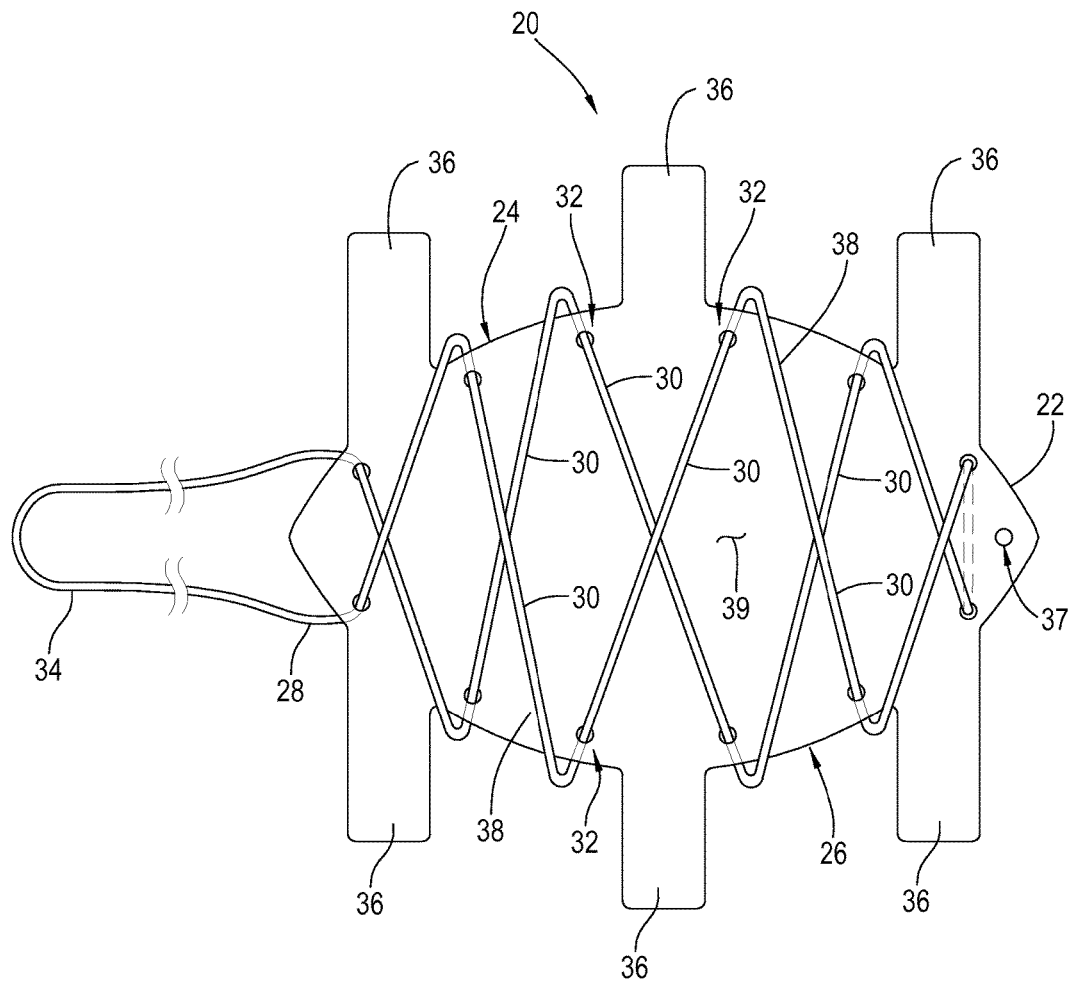
FIG. 1 provides a top view of one embodiment of a surgical graft.

For the purpose of promoting an understanding of the principles of the invention, reference will now be made to embodiments, some of which are illustrated in the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

With reference now to FIG. 1, shown is one embodiment of a graft device 20 in accordance with the invention. Graft device 20 is generally formed as a patch and includes a sheet form graft body 22 having a first convexly curved lateral edge 24 and a second convexly curved lateral edge 26 opposite to the first edge 24. Edges 24 and 26 are configured to extend adjacent to or along anterior and posterior tonsillar pillars of a patient, especially a human patient. Device 20 also includes a pull tether 28, which is preferably resorbable, and which for example can be suitably made from suture material. The pull tether 28 is associated with the graft body 22 such that tensioning tether 28 re-shapes graft body 22, desirably causing a folding of graft body and consequent movement of edges 24 and 26 toward one another. In the illustrated embodiment pull tether 28 includes a plurality of tether segments 30 extending generally from a region proximate to lateral edge 24 to a region proximate to lateral edge 26. This is accomplished by lacing pull tether 28 through apertures 32. Tether 28 includes a segment or region 34 that is spaced from the body 22 and configured to be pulled to re-shape the graft body 22. Optionally, as shown, segment or region 34 can be a looped region. Graft body 22 in certain embodiments also includes buttress segments 36 extending outwardly from edges 24 and 26 respectively. Buttress segments 36 are positioned and configured for buttressing a stitch that connects the anterior and posterior tonsillar pillars after they are drawn together, as discussed further hereinbelow. Graft body 22 also includes suture-receiving regions 38 that occur between apertures 32. These regions are operable to receive and support sutures that attach the body 22 to patient tissue proximate to the surgical defect to be treated, as further discussed hereinbelow. Graft device 20 also includes a mounting aperture 37 proximate one end thereof, which can be used to assist in mounting the device 20 to a delivery implement. As shown, device 20 includes a graft surface 39 over which exposed tether segments 30 are received.

Figure 2A:
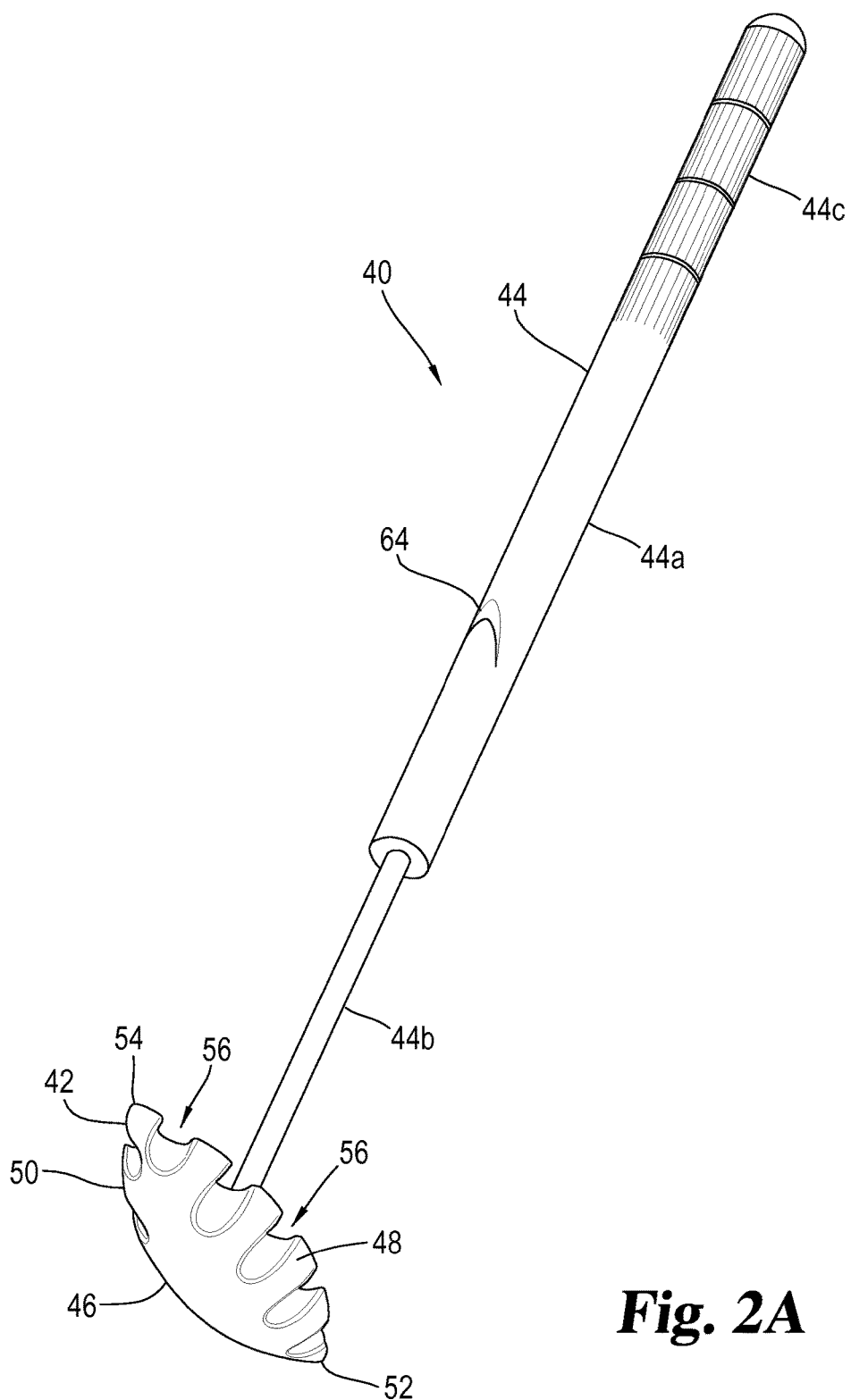
FIG. 2A provides a perspective view of one embodiment of a graft delivery implement.

Embodiments of the invention also provide a delivery implement useful for delivering a graft device such as device 20 described above. With reference to FIGS. 2A, 2B, and 2C, shown is graft delivery implement 40. Delivery implement 40 includes a delivery head 42 and a handle 44 attached thereto. Handle 44 preferably includes a first handle section 44a which is generally rigid and a second handle section 44b which is bendable or otherwise deformable so as to hold a modified shape (e.g. a bend or corner) during delivery, which can provide enhanced ergonomics. In certain forms, handle section 44b can be made from or can incorporate (e.g. embedded in plastic) a malleable metal member, such as a malleable wire, for these purposes. Handle 44 can also include a roughened grip region 44c. Delivery head 42 includes a convexly curved forward face 46, preferably a complexly curved or other bulbous surface. Delivery head 42 includes a first lateral side 48 and second lateral side 50 opposed thereto. Delivery head 42 also includes a first end surface 52 and a second end surface 54 opposed thereto. Preferably, as shown, delivery head 42 has a generally symmetrically shape. Delivery head 42 also defines a plurality of open-sided slots 56 at spaced locations along side 48 and side 50 respectively. Slots 56 are open to the periphery of sides 48 and 50 and also to a rearward surface 62 of delivery head 42. Slots 56 have rounded back or inner walls 60. Implement 40 also includes a tether-engaging slot 64 defined in handle 44, and a graft mounting barb 66, preferably a curved barb curving inward toward handle 44 or the central region of head 42, adjacent end surface 52 thereof.

Figure 3:
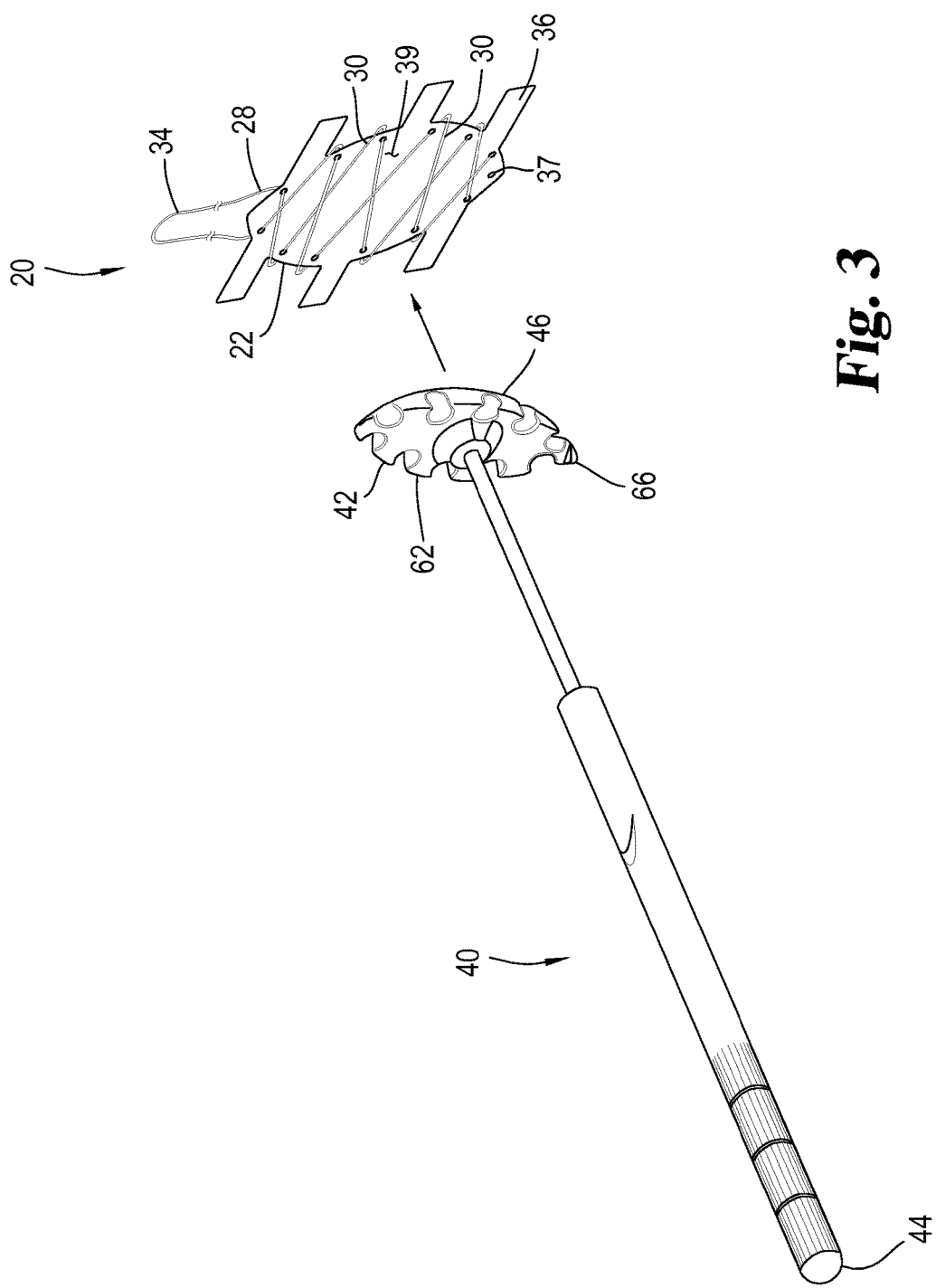
FIG. 3 provides a perspective view of the implement of FIGS. 2A-2C in the process of mounting to the surgical graft of FIG. 1.
Figure 4:
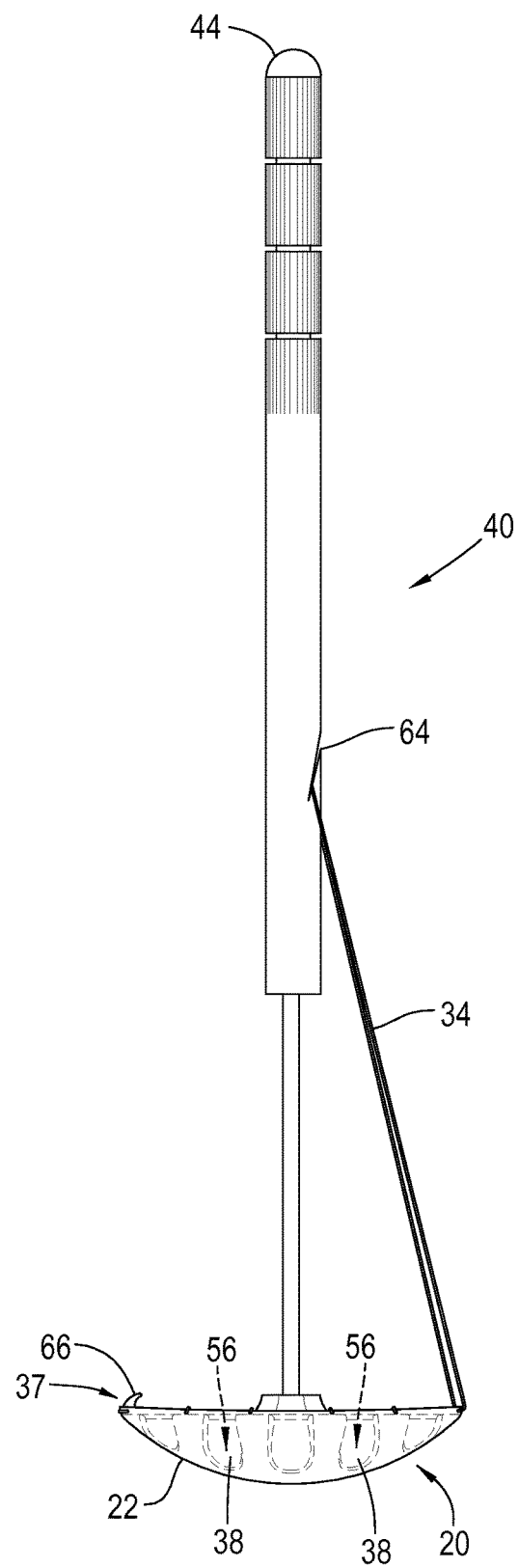
FIG. 4 provides a side view of a graft delivery device including the graft of FIG. 1 mounted on the implement of FIGS. 2A-2C.

With reference now to FIGS. 3 and 4 the combination and mounting of graft device 20 upon delivery head 42 of delivery implement 40 to form a grafting apparatus will now be discussed. As shown in FIG. 3, the forward surface 46 of delivery head 42 is maneuvered into contact with the face 39 of the graft device 20 that bears the exposed lacing pattern of tether 28. Aperture 37 is maneuvered to receive barb 66 there around, and the graft device 20 is positioned against forward surface 46 and tether region 34 is tensioned so as to draw graft device sides 24 and 26 toward one another and thereby securely wrap the graft device 20 over and around the delivery head 42 of delivery implement 40 (see FIG. 4). Tether region 34 can then be secured within slot 64 on delivery implement handle 44 under tension. In this manner, graft 20 will be securely held in position over delivery head 42. When so constructed, graft body suture-receiving regions 38 are suspended over suture guide slots 56 of delivery head 42.

Figure 5:
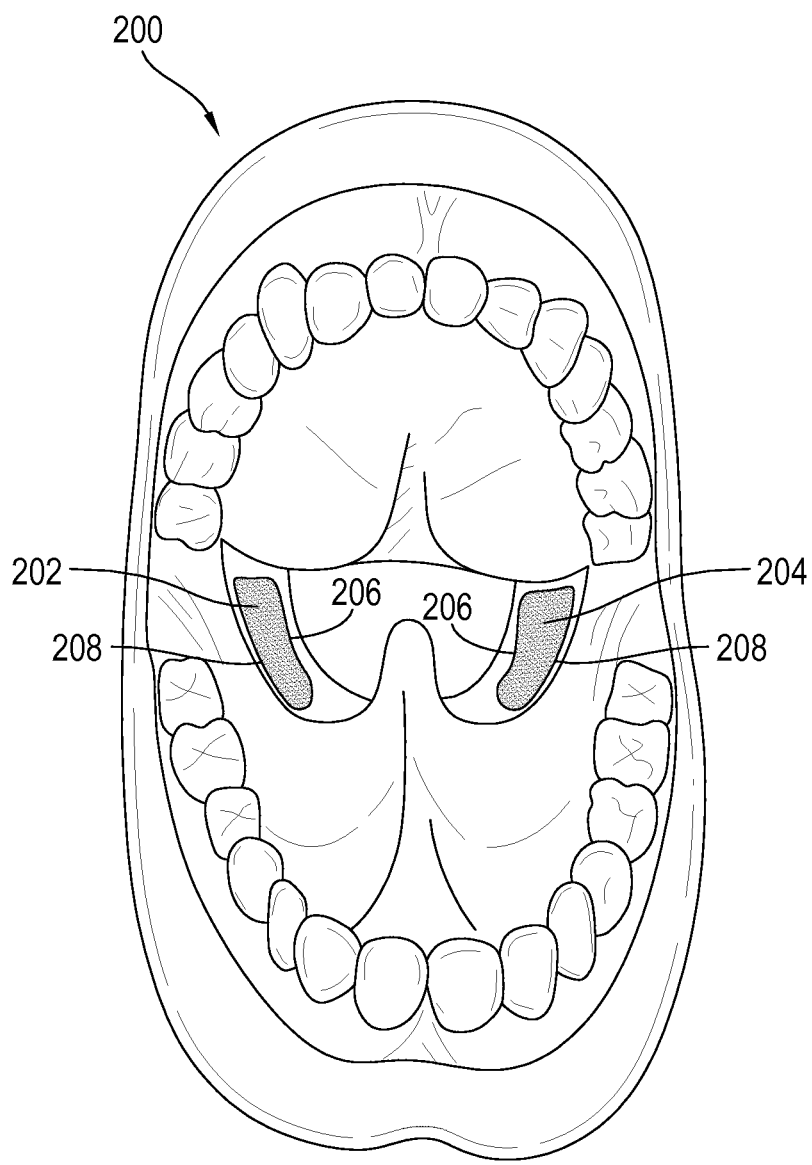
FIG. 5 provides an illustration of a patient mouth having tonsillectomy surgical defects spanning between anterior and posterior tonsillar pillars.
Figure 6:
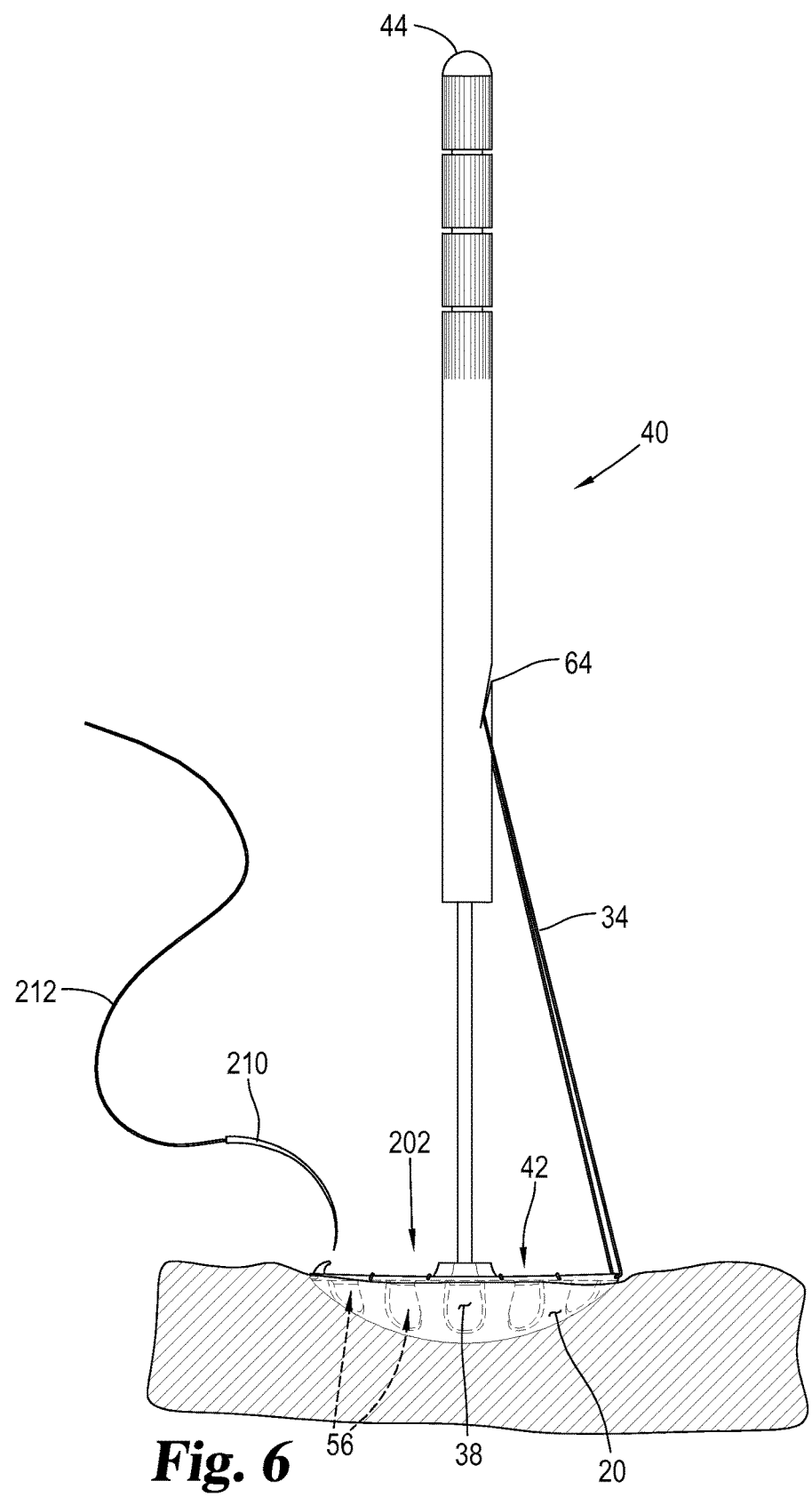
FIG. 6 provides a cutaway view of the graft delivery device of FIG. 4 in use to apply the surgical graft to a tonsillectomy surgical defect.
Figure 7:
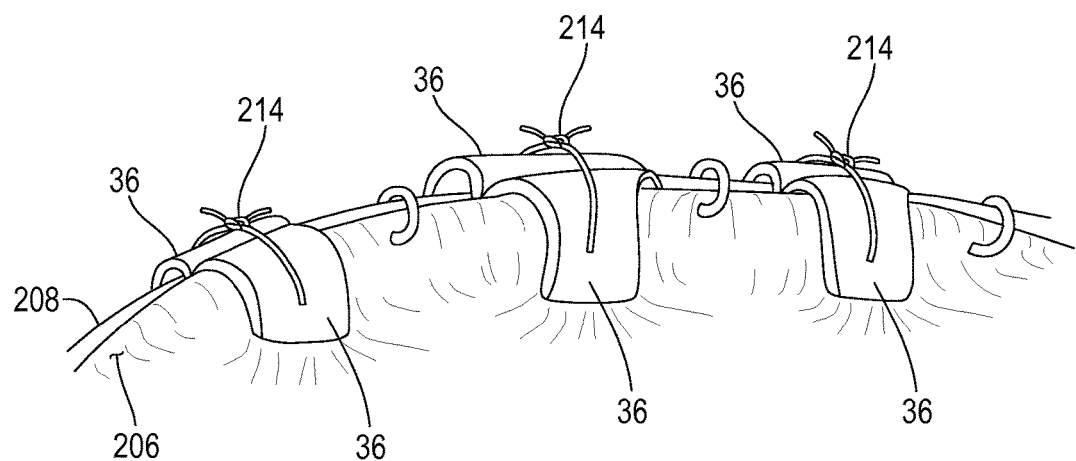
FIG. 7 provides an illustration of a grafted, closed and buttressed tonsillectomy defect where the anterior and posterior tonsillar pillars have been approximated together.

With reference now to FIGS. 5, 6 and 7, in conjunction with the other Figures, one illustrative use of the assembled graft delivery apparatus shown in FIG. 4 will be described. FIG. 5 is an illustration of a patient mouth 200 having surgical defects 202 and 204 created by removal of tonsils and surrounding tissues. This removal may occur, for example, in a tonsillectomy procedure. Such a procedure can be performed by any suitable method, and for any of a variety of reasons. For example, the procedure may be performed by an electrocautery, bipolar radiofrequency (RF), cold knife, powered intracapsular, or ultrasonic dissection technique. The procedure may be performed on a child or an adult. Adult tonsillectomies are conducted for a variety of reasons, including for example where a patient experiences frequent bouts of acute tonsillitis, has repeated bouts of peritonsillar abscess, has sleep apnea, has difficulty eating or swallowing due to enlarged tonsils, produces tonsilloliths in the back of their mouth, or has abnormally large tonsils with crypts. It is sometimes desirable in a tonsillectomy to draw the anterior and posterior tonsillar pillars together. Illustratively, tonsillectomy is sometimes performed in uvulopalatopharyngoplasty (also known by the abbreviations UPPP and UP3), a surgical procedure used to remove tissue in the throat, for example to treat sleep apnea. Graft devices and methods described herein can, for example, be used in the performance of any such tonsillectomy procedures, or others. In certain aspects, the grafts may for example aid in hemostasis, healing, and/or reducing the post-procedural pain experienced by the patient.

Defects 202 and 204 occur between posterior tonsillar pillar 206 and anterior tonsillar pillar 208 of the patient. Referring particularly now to FIG. 6, shown is a cutaway view of the assembled graft delivery apparatus of FIG. 4 in use to deliver graft device 20 to a tonsillectomy surgical defect, for example defects 202 and/or defect 204. As shown, delivery head 42 is guided to press the graft device 20 against a defect using handle 44. The curved forward face 46 of head 42 thereby presses graft device 20 into the defect, thus covering the defect. In this regard, delivery head 42 desirably has a maximum width in the direction from lateral side 48 to lateral side 50 that is about equal to or less than the width between posterior and anterior tonsillar pillars 206 and 208, so that the head 42 can be fit between the pillars. With the graft device 20 held in position by implement 40, the physician or other attending healthcare provider can attach the graft device 20 to the surrounding patient tissues. This can be accomplished in one mode by using a needle, such as curved needle 210, and suture material 212. This needle/suture combination can be used to apply a running suture attaching edge 24 to surrounding patient tissue, and a similar needle/suture arrangement can be used to attach edge 26 to surrounding patient tissue. When applying these sutures, the physician or other healthcare provider can insert needle 210 into respective ones of needle guide slots 56 (shown in phantom, FIG. 6), through the securement region 38 of graft body 22 suspended thereover, through patient tissue, and then on into the next adjacent slot 56. This process can be repeated to apply a running suture as discussed above. It will be understood that other suture patterns can be applied, including single stitches, running sutures, and combinations thereof. Similarly, connectors other than sutures can be used to attach the graft device 20 to the patient tissue.

After attachment of the graft device 20 the patient tissue is complete, the tether region 34 can be removed from slot 64, and the delivery implement 40 can be removed from contact with the graft device 20. The delivery implement can be cleared from the patient's mouth. At this point, tether region 34 can be tensioned and in so doing the edges 24 and 26 of the graft body will be drawn toward one another in a folding movement and in turn this will draw the posterior and anterior tonsillar pillars toward one another since the graft device body 22 is attached to patient tissues with sutures or other means as discussed above. With the pillars drawn together, tether 28 can be secured, for example by tying it off or stitching, to hold the pillars in position together. In this manner, the surgical defect can both be covered with graft device 20 and closed. With reference to FIG. 7, shown is such a closed condition for this surgical defect having anterior and posterior tonsillar pillars 206 and 208 adjacent to one another. At this point, the buttress segments 36 can be folded over their respective adjacent tonsillar pillars, and can be used as buttressing materials for additional stitches 214 passed through the tonsillar pillars to aid in securing them together. Any suitable stitch pattern can be used, including for example continuous or running stitches or individual stitches. Likewise, other connectors can be used to connect the pillars together through buttressing segments 36.

Figure 8:
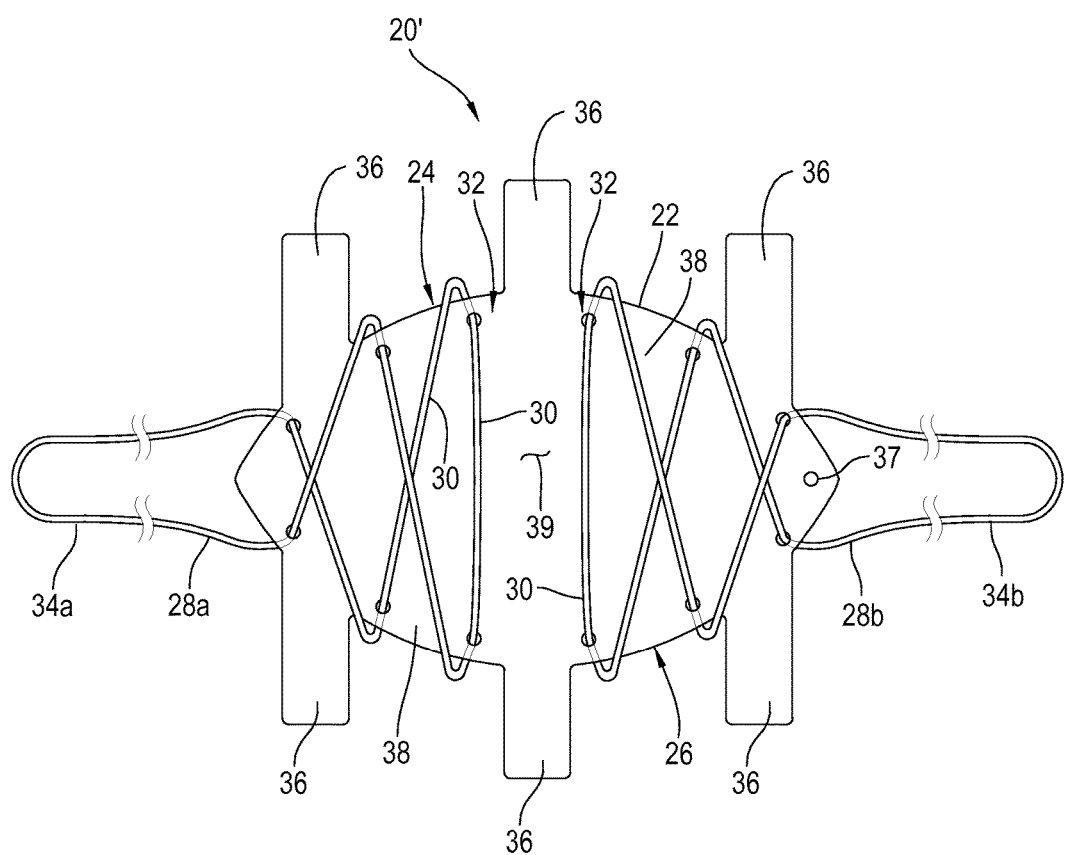
FIG. 8 provides a top view of an alternative embodiment of a surgical graft.

FIG. 8 provides an illustration of an alternative graft device 20', similar to graft device 20 and including similar features which bear the same designation numbers. However, graft device 20' incorporates an alternative pull tether arrangement. Graft device 20' includes two independent pull tethers 28a and 28b, each of which serves to reshape a segment of the graft body 22 with which it is associated. Pull tethers 28a and 28b can include respective regions 34a and 34b (e.g. looped regions as shown), which can be pulled to reshape the graft body 22 and move edge 24 toward edge 26 as the graft body 22 folds. Graft device 20' can optionally be mounted to and used in conjunction with a graft delivery implement such as implement 40 described herein. In so doing, tether regions 34a and 34b can be secured in a single engagement slot (e.g. 64) or separate slots can be provided on the delivery implement.

Graft materials used in the invention to form the graft body (e.g. 22) can include a decellularized animal tissue layer, typically including extracellular matrix (ECM) tissue. The ECM or other tissue layer can be obtained from a warm-blooded vertebrate animal, such as an ovine, bovine or porcine animal. For example, suitable ECM tissue include those comprising submucosa, renal capsule membrane, dermal collagen, dura mater, pericardium, amnion, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. ECM tissues comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source. Porcine tissue sources are preferred sources from which to harvest ECM tissues, including submucosa-containing ECM tissues.

ECM tissue when used in the invention is preferably decellularized and highly purified, for example, as described in U.S. Pat. No. 6,206,931 to Cook et al. or U.S. Patent Application Publication No. US2008286268 dated Nov. 20, 2008, publishing U.S. patent application Ser. No. 12/178, 321 filed Jul. 23, 2008, all of which are hereby incorporated herein by reference in their entirety. Preferred ECM tissue material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 or U.S. Patent Application Publication No. US2008286268 may be characteristic of any ECM tissue used in the present invention.

In certain embodiments, the ECM tissue material used as or in the cell growth substrate will be a membranous tissue with a sheet structure as isolated from the tissue source. The ECM tissue can, as isolated, have a layer thickness that ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source.

The ECM tissue material utilized desirably retains a structural microarchitecture from the source tissue, including structural fiber proteins such as collagen and/or elastin that are non-randomly oriented. Such non-random collagen and/or other structural protein fibers can in certain embodiments provide an ECM tissue that is non-isotropic in regard to tensile strength, thus having a tensile strength in one direction that differs from the tensile strength in at least one other direction.

The ECM tissue material may include one or more bioactive agents native to the source of the ECM tissue material and retained in the ECM tissue material through processing. For example, a submucosa or other remodelable ECM tissue material may retain one or more native growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other native bioactive agents such as but not limited to proteins, glycoproteins, proteoglycans, and glycosaminoglycans. For example, ECM materials may include heparin, heparin sulfate, hyaluronic acid, fibronectin, cytokines, and the like. Thus, generally speaking, a submucosa or other ECM material may retain from the source tissue one or more bioactive components that induce, directly or indirectly, a cellular response such as a change in cell morphology, proliferation, growth, protein or gene expression. In certain aspects, a retained growth factor (e.g. FGF-2) or other bioactive agent can promote the invasion of patient tissue into the graft body and thereby speed the attachment, and potentially the eventual incorporation, of the graft body to patient tissue.

Submucosa-containing or other ECM materials used in the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa-containing or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of such native bioactive components, non-native bioactive components such as those synthetically produced by recombinant technology or other methods (e.g., genetic material such as DNA), may be incorporated into an ECM or other graft material used in the invention. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to materials include, for example, antibiotics, analgesics (e.g. bupivicaine or lidocaine) anti-inflammatory agents, thrombus-promoting substances such as blood clotting factors, e.g., thrombin, fibrinogen, and the like. In other embodiments, an adhesive may be applied to an outer surface of the graft, for example in a location to contact patient tissue (for example to the patient-contacting surface graft 20 or 20' opposite surface 39), to facilitate adherence of the graft to the patient tissue, and/or in a location to facilitate temporary (releasable) adherence of the graft to a delivery implement (e.g. to all or portions of surface 39 of graft 20 or 20'). Such non-native bioactive components can be incorporated into and/or onto ECM material in any suitable manner, for example, by surface treatment (e.g., spraying) and/or impregnation (e.g., soaking), just to name a few. Also, these substances may be applied to the ECM material in a premanufacturing step, immediately prior to the procedure (e.g., by soaking the material in a solution containing a suitable antibiotic), or during or after administration of the graft to the patient.

Inventive grafts herein can incorporate xenograft ECM material (i.e., cross-species material, such as tissue material from a non-human donor to a human recipient), allograft ECM material (i.e., interspecies material, with tissue material from a donor of the same species as the recipient), and/or autograft ECM material (i.e., where the donor and the recipient are the same individual). Further, any exogenous bioactive substances incorporated into an ECM material may be from the same species of animal from which the ECM material was derived (e.g. autologous or allogenic relative to the ECM material) or may be from a different species from the ECM material source (xenogenic relative to the ECM material). In certain embodiments, ECM tissue material will be xenogenic relative to the patient receiving the graft, and any added cells or other exogenous material(s)

will be from the same species (e.g. autologous or allogenic) as the patient receiving the graft. Illustratively, human patients may be treated with xenogenic ECM materials (e.g. porcine-, bovine- or ovine-derived) that have been modified with exogenous human cells and/or serum proteins and/or other material(s) as described herein, those exogenous materials being naturally derived and/or recombinantly produced.

When used in the invention, ECM materials can be free or essentially free of additional, non-native crosslinking, or may contain additional crosslinking. Such additional crosslinking may be achieved by photo-crosslinking techniques, by chemical crosslinkers, or by protein crosslinking induced by dehydration or other means. However, because certain crosslinking techniques, certain crosslinking agents, and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

In additional embodiments, grafts of the invention can be made from ECM's or other collagenous materials that have been subjected to processes that expand the materials. In certain forms, such expanded materials can be formed by the controlled contact of an ECM material with a denaturing agent such as one or more alkaline substances until the material expands, and the isolation of the expanded material. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of a substrate. Illustratively, the expanded material can be enriched with bioactive components, comminuted, dried, and/or molded, etc., in the formation of a substrate of a desired shape or configuration. In certain embodiments, a dried substrate formed with the expanded ECM material can be highly compressible and/or expandable.

Treatment of an ECM material with a denaturant, such as an alkaline material, can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. It will be apparent to one skilled in the art that the magnitude of the expansion is related to several factors, including for instance the concentration or pH of the alkaline medium, the exposure time of the alkaline medium to the material, and temperature used in the treatment of the material to be expanded, among others. These factors can be varied through routine experimentation to achieve a material having the desired level of expansion, given the disclosures herein.

A collagen fibril is comprised of a quarter-staggered array of tropocollagen molecules. The tropocollagen molecules themselves are formed from three polypeptide chains linked together by covalent intramolecular bonds and hydrogen bonds to form a triple helix. Additionally, covalent intermolecular bonds are formed between different tropocollagen molecules within the collagen fibril. Frequently, multiple collagen fibrils assemble with one another to form collagen fibers. It is believed that the addition of an alkaline substance to the material as described herein can be conducted so as to not significantly disrupt the intramolecular and intermolecular bonds, but denature the material to an extent that provides to the material an increased processed thickness, e.g. at least twice the naturally-occurring thickness. ECM materials that can be processed to make expanded materials for use as substrates can include any of those disclosed herein or other suitable ECM's. Typical such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness. The expanded ECM material can then be processed to provide foam or sponge substrates for use as or in the graft body, e.g. by comminuting, casting, and drying the processed material. Additional information concerning expanded ECM materials and their preparation is found in United States Patent Application Publication No. US20090326577 published Dec. 31, 2009, publishing U.S. patent application Ser. No. 12/489,199 filed Jun. 22, 2009, which is hereby incorporated herein by reference in its entirety.

In addition to or as an alternative to ECM materials, the graft used in the invention may be comprised of other suitable materials. Illustrative materials include, for example, synthetically-produced substrates comprised or natural or synthetic polymers. Illustrative synthetic polymers are preferably biodegradable synthetic polymers such as polylactic acid, polyglycolic acid or copolymers thereof, polyanhydride, polycaprolactone, polyhydroxy-butyrate valerate, polyhydroxyalkanoate, or another biodegradable polymer or mixture thereof. Preferred graft bodies comprised of these or other materials (e.g. ECM materials as discussed herein) will be porous matrix materials configured to allow cellular invasion and ingrowth into the matrix.

ECM or other biocompatible layers can be used in the invention as single layer constructs, but in certain advantageous embodiments will be used in multilaminate constructs. In this regard, a variety of techniques for laminating layers together are known and can be used to prepare multilaminate constructs used for the graft in the present invention. For example, a plurality of (i.e. two or more) layers of collagenous material, for example submucosa-containing or other ECM material, can be bonded together to form a multilaminate structure. Illustratively, two, three, four, five, six, seven, or eight or more collagenous layers containing submucosal or other collagenous ECM materials can be bonded together to provide a multilaminate collagenous substrate material for use in the present invention. In certain embodiments, two to eight, more preferably two, three or four, collagenous, submucosa-containing layers isolated from a warm-blooded vertebrate are bonded together to form a multilaminate graft. Preferably such submucosa-containing layers are isolated from intestinal tissue, more preferably small intestinal tissue. Porcine-derived tissue is preferred for these purposes. The layers of collagenous tissue can be bonded together in any suitable fashion, including dehydrothermal bonding under heated, non-heated or lyophilization conditions, using adhesives, glues or other bonding agents, crosslinking with chemical agents or radiation (including UV radiation), or any combination of these with each other or other suitable methods. For additional information as to multilaminate ECM constructs that can be used in the invention, and methods for their preparation, reference may be made for example to U.S. Pat. Nos. 5,711,969, 5,755,791, 5,855,619, 5,955,110, 5,968,096, and to U.S. Patent Publication No. 20050049638 A1 published Mar. 3, 2005. These constructs can be perforated or non-perforated, and when perforated may include an array of perforations extending substantially across the surface of the construct, or may include perforations only in selected areas.

The graft delivery implement, such as implement 40, can be made of any suitable material. For example, it may be made from a suitable polymeric material, metal, ceramic, or any combination thereof with each other or other suitable materials. It may be manufactured by any suitable technique such as molding, forming, machining, or combinations thereof.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. A surgical tonsillectomy method, comprising:
    removing tissue from a patient, the tissue including at least one tonsil, so as to create a surgical defect between a posterior tonsillar pillar and an anterior tonsillar pillar of the patient;
    applying to the surgical defect a graft including a sheet-form decellularized animal tissue layer comprising extracellular matrix tissue said graft positioned such that a first lateral edge of the graft is adjacent the anterior tonsillar pillar and a second lateral edge of the graft opposite said first lateral edge is adjacent the posterior tonsillar pillar, wherein said graft includes a first plurality of buttress segments extending from said first lateral edge and sized to extend over the anterior tonsillar pillar, a second plurality of buttress segments extending from said second lateral edge and sized to extend over the posterior tonsillar pillar, and wherein said first plurality of buttress segments and said second plurality of buttress segments comprise portions of said sheet-form decellularized animal tissue layer comprising extracellular matrix tissue, each of said buttress segments having a first sheet face between a first buttress edge and a second buttress edge and a second sheet face opposite said first sheet face and between said first buttress edge and said second buttress edge, wherein said buttress segments are configured to fold over and cover segments of the anterior or posterior tonsillar pillars and receive a stitch through the buttress segment and underlying pillar segment;
    closing the surgical defect by bringing together said first lateral edge and said second lateral edge so as to draw the posterior tonsillar pillar and the anterior tonsillar pillar toward one another; and
    securing the closed surgical defect by passing a stitch through one or more of the buttress segments and the underlying pillar segments.

2. The method of claim 1, wherein the graft comprises a multilaminate construct including a plurality of layers of said decellularized animal tissue layer.

3. The method of claim 2, wherein the decellularized animal tissue layers are dehydrothermally bonded to one another.

4. The method of claim 1, wherein the decellularized animal tissue layer retains at least one native growth factor of the tissue layer.

5. The method of claim 1, wherein the graft comprises a graft body and one or more tethers connected to the graft body and operable upon tensioning to move said first lateral edge and said second lateral edge of the graft body toward one another.

6. The method of claim 5, wherein said one or more tethers includes a plurality of pull tethers.

7. The method of claim 6, wherein said plurality of pull tethers includes tethers laced between multiple positions proximate to the first lateral edge and multiple positions proximal to the second lateral edge.

8. The method of claim 1, also comprising:
    securing the graft to the surgical defect; and
    tensioning a tether connected to the graft so as to fold the graft and thereby fold the defect.

9. The method of claim 1, wherein said first lateral edge is convexly curved and said second lateral edge is convexly curved.

10. The method of claim 1, wherein said first lateral edge and said second lateral edge are convexly curved.

11. The method of claim 1, wherein said applying step further comprises introducing the graft while in contact with a graft delivery implement, the graft delivery implement comprising:
    a handle;

a delivery head connected to the handle and sized and configured for receipt onto a tonsillectomy defect between the anterior tonsillar pillar and the posterior tonsillar pillar; and the delivery head including:
a forward face for receiving the graft;
a first lateral delivery head region including a first plurality of open-sided suturing slots extending inward from an outer edge of the first lateral delivery head region; and
a second lateral delivery head region opposite the first lateral delivery head region, the second lateral delivery head region including a second plurality of open-sided suturing slots extending inward from an outer edge of the second lateral delivery head region.

12. The method of claim 11, wherein the forward face of the delivery head has a convexly curved surface.

13. The method of claim 11, wherein said delivery head also comprises a barb member for engaging the graft.

14. The method of claim 11, wherein the graft delivery implement also comprises a tether retention slot defined in the handle.

15. The method of claim 11, wherein said first plurality of open-sided suturing slots and said second plurality of open-sided suturing slots terminate inwardly at rounded inner slot walls.

16. The method of claim 11, wherein the outer edge of the first lateral delivery head region and the outer edge of the second lateral delivery head region are each convexly curved.

17. A surgical tonsillectomy method, comprising:
removing tissue from a patient, the tissue including at least one tonsil, so as to create a surgical defect between a posterior tonsillar pillar and an anterior tonsillar pillar of the patient;
applying to the surgical defect a graft including a sheet-form decellularized animal tissue layer comprising extracellular matrix tissue, said graft positioned such that a first lateral edge of the graft is adjacent the anterior tonsillar pillar and a second lateral edge of the graft opposite said first lateral edge is adjacent the posterior tonsillar pillar, wherein said graft includes a first plurality of buttress segments extending from said first lateral edge and sized to extend over the anterior tonsillar pillar, a second plurality of buttress segments extending from said second lateral edge and sized to extend over the posterior tonsillar pillar, and wherein said first plurality of buttress segments and said second plurality of buttress segments comprise portions of said sheet-form decellularized animal tissue layer comprising extracellular matrix tissue, wherein each of said buttress segments having a first sheet face extending between a first buttress edge and a second buttress edge and a second sheet face opposite said first sheet face and between said first buttress edge and said second buttress edge, and wherein said buttress segments are configured to receive a stitch passing through the buttress segments and the underlying tonsillar pillars;
wherein said applying is conducted with the graft in contact with a graft delivery implement, the graft delivery implement comprising:
a handle;
a delivery head connected to the handle and sized and configured for receipt onto a tonsillectomy defect between the anterior tonsillar pillar and the posterior tonsillar pillar; and
the delivery head including:
a forward face for receiving the graft;
a first lateral delivery head region on a first side of said forward face including a first plurality of open-sided suturing slots extending inward from an outer edge of the first lateral delivery head region;
a second lateral delivery head region on a second side of said forward face and opposite the first lateral delivery head region, the second lateral delivery head region including a second plurality of open-sided suturing slots extending inward from an outer edge of the second lateral delivery head region; and
an intermediate delivery head region occurring laterally between the first lateral delivery head region and the second lateral delivery head region, the intermediate delivery head region defining a convexly curved surface; and
attaching the graft to the surgical defect such that the sheet-form decellularized animal tissue layer contacts the surgical defect, wherein said attaching comprises passing one or more sutures through the first plurality of open-sided suturing slots and/or the second plurality of open-sided suturing slots and through the graft and underlying patient tissue;
closing the surgical defect by bringing together said first lateral edge and said second lateral edge so as to draw the posterior tonsillar pillar and the anterior tonsillar pillar toward one another.

18. The method of claim 17, wherein the extracellular matrix tissue comprises submucosal tissue.

19. The method of claim 17, wherein the graft comprises a multilaminate construct including a plurality of layers of said decellularized animal tissue layer.

20. The method of claim 19, wherein the decellularized animal tissue layers are dehydrothermally bonded to one another.

21. The method of claim 17, wherein the graft comprises a graft body and one or more tethers connected to the graft body and operable upon tensioning to move said first lateral edge and said second lateral edge of the graft body toward one another.

22. The method of claim 21, wherein said one or more tethers includes a plurality of pull tethers.

23. The method of claim 22, wherein said plurality of pull tethers includes tethers laced between multiple positions proximate to the first lateral edge and multiple positions proximal to the second lateral edge.

24. The method of claim 17, also comprising:
securing the graft to the surgical defect; and
tensioning a tether connected to the graft so as to fold the graft and thereby fold the defect.

25. The method of claim 17, wherein said first lateral edge is convexly curved and said second lateral edge is convexly curved.

26. The method of claim 17, wherein said decellularized animal tissue layer includes one or more of submucosa, renal capsule membrane, dermal collagen, dura mater, pericardium, amnion, fascia lata, serosa, peritoneum or basement membrane.

27. The method of claim 17, wherein the forward face of the delivery head has a convexly curved surface.

28. The method of claim 17, wherein said delivery head also comprises a barb member for engaging the graft.

29. The method of claim 17, wherein the graft delivery implement also comprises a tether retention slot defined in the handle.

30. The method of claim 17, wherein the outer edge of the first lateral delivery head region and the outer edge of the second lateral delivery head region are each convexly curved.

31. The method of claim 17, wherein said first plurality of open-sided suturing slots and said second plurality of open-sided suturing slots terminate inwardly at rounded inner slot walls.

\* \* \* \* \*